US010684239B2

(12) United States Patent
Koseoglu et al.

(10) Patent No.: US 10,684,239 B2
(45) Date of Patent: Jun. 16, 2020

(54) CHARACTERIZATION OF CRUDE OIL BY NMR SPECTROSCOPY

(71) Applicant: Saudi Arabian Oil Company, Dhahran (SA)

(72) Inventors: Omer Refa Koseoglu, Dhahran (SA); Adnan Al-Hajji, Dhahran (SA); Mohammed Abdullah Al-Ghamdi, Dhahran (SA); Alexander Rebrov, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 24 days.

(21) Appl. No.: 15/639,345

(22) Filed: Jun. 30, 2017

(65) Prior Publication Data

US 2018/0011037 A1  Jan. 11, 2018

Related U.S. Application Data

(63) Continuation-in-part of application No. PCT/US2016/012115, filed on Jan. 5, 2016, and a continuation-in-part of application No. 13/397,273, filed on Feb. 15, 2012, now abandoned.

(60) Provisional application No. 62/099,677, filed on Jan. 5, 2015, provisional application No. 61/445,175, filed on Feb. 22, 2011.

(51) Int. Cl.
*G01N 24/08* (2006.01)
*G01N 33/28* (2006.01)
*G01R 33/46* (2006.01)

(52) U.S. Cl.
CPC ....... *G01N 24/081* (2013.01); *G01N 33/2829* (2013.01); *G01R 33/46* (2013.01); *G01R 33/4625* (2013.01)

(58) Field of Classification Search
None
See application file for complete search history.

(56) References Cited

U.S. PATENT DOCUMENTS

| 3,617,501 A | 11/1971 | Eng |
| 3,896,312 A | 7/1975 | Brown |
| 4,251,870 A | 2/1981 | Jaffe |

(Continued)

FOREIGN PATENT DOCUMENTS

| CA | 2781273 A1 | 12/2013 |
| EP | 0305090 A2 | 8/1988 |

(Continued)

OTHER PUBLICATIONS

Miknis, F. P. and Netzel, D. A. (2006). Nuclear Magnetic Resonance Characterization of Petroleum. In Encyclopedia of Analytical Chemistry (eds R. A. Meyers and P. A. Nick). doi:10.1002/9780470027318. a1828 (Year: 2006).*

(Continued)

*Primary Examiner* — Lina M Cordero
(74) *Attorney, Agent, or Firm* — Abelman, Frayne and Schwab

(57) ABSTRACT

A system and a method for applying $^{13}C$ or $^{1}H$ NMR spectroscopy to a sample of oil in order to calculate and assign an indicative property such as cetane number, pour point, cloud point, aniline point and/or octane number of a gas oil or naphtha fraction of the crude oil.

21 Claims, 3 Drawing Sheets

(56) References Cited

U.S. PATENT DOCUMENTS

| | | | |
|---|---|---|---|
| 4,711,968 A * | 12/1987 | Oswald | C07C 29/16 568/454 |
| 4,897,177 A | 1/1990 | Nadler | |
| 4,914,246 A * | 4/1990 | Oswald | B01F 17/0028 568/788 |
| 4,922,028 A * | 5/1990 | Oswald | C07C 29/16 568/448 |
| 4,971,915 A | 11/1990 | Schwartz et al. | |
| 4,973,764 A * | 11/1990 | Oswald | B01F 17/0028 568/630 |
| 4,988,446 A | 1/1991 | Haberman | |
| 5,030,774 A * | 7/1991 | Oswald | C07C 29/16 568/454 |
| 5,072,057 A * | 12/1991 | Oswald | C07C 29/16 568/454 |
| 5,121,337 A | 6/1992 | Brown | |
| 5,223,714 A | 6/1993 | Maggard | |
| 5,266,800 A | 11/1993 | Mullins | |
| 5,304,807 A | 4/1994 | Lin | |
| 5,349,188 A * | 9/1994 | Maggard | G01N 21/359 250/339.12 |
| 5,424,959 A | 6/1995 | Reyes | |
| 5,452,232 A | 9/1995 | Espinosa et al. | |
| 5,475,612 A | 12/1995 | Espinosa | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 5,699,270 A | 12/1997 | Ashe et al. | |
| 6,070,128 A | 5/2000 | Descales | |
| 6,258,987 B1 | 7/2001 | Schmidt et al. | |
| 6,275,775 B1 | 8/2001 | Baco | |
| 6,490,029 B1 | 12/2002 | Cho | |
| 6,602,403 B1 | 8/2003 | Steffens et al. | |
| 6,611,735 B1 | 8/2003 | Henly | |
| 6,633,043 B2 | 10/2003 | Hegazi | |
| 6,662,116 B2 | 12/2003 | Brown | |
| 6,711,532 B1 | 3/2004 | Spieksma | |
| 6,841,779 B1 | 1/2005 | Roehner et al. | |
| 6,893,874 B2 | 5/2005 | Stark | |
| 7,126,332 B2 | 10/2006 | Blanz | |
| 7,173,239 B2 | 2/2007 | DiFoggio | |
| 7,560,711 B2 | 7/2009 | Hegazi | |
| 7,598,487 B2 | 10/2009 | Qian | |
| 8,714,246 B2 | 5/2014 | Pop et al. | |
| 8,930,149 B1 | 1/2015 | Koseoglu et al. | |
| 9,285,307 B2 | 3/2016 | Koseoglu et al. | |
| 9,423,391 B2 | 8/2016 | Koseoglu et al. | |
| 9,429,556 B2 | 8/2016 | Koseoglu et al. | |
| 9,778,240 B2 | 10/2017 | Koseoglu et al. | |
| 9,816,919 B2 | 11/2017 | Koseoglu et al. | |
| 2002/0052769 A1 | 5/2002 | Navani et al. | |
| 2003/0141459 A1 | 7/2003 | Hegazi et al. | |
| 2003/0195708 A1 | 10/2003 | Brown | |
| 2005/0109934 A1 | 5/2005 | David | |
| 2005/0173298 A1 | 8/2005 | Wellington | |
| 2006/0043004 A1 | 3/2006 | Rose | |
| 2006/0047444 A1 | 3/2006 | Brown | |
| 2006/0142955 A1 | 6/2006 | Jones | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0037006 A1 | 2/2008 | Canas Triana | |
| 2008/0040051 A1 | 2/2008 | Franklin et al. | |
| 2008/0206887 A1 | 8/2008 | Chen | |
| 2008/0248967 A1 | 10/2008 | Butler et al. | |
| 2008/0253426 A1 | 10/2008 | Voelkening | |
| 2008/0260584 A1 | 10/2008 | Gudde et al. | |
| 2009/0011517 A1 | 1/2009 | Hodges | |
| 2009/0180949 A1 | 7/2009 | Cui | |
| 2009/0279072 A1 | 11/2009 | Arakawa | |
| 2009/0290144 A1 | 11/2009 | Hegazi | |
| 2009/0316139 A1 | 12/2009 | Shrestha | |
| 2010/0049681 A1 | 2/2010 | Pradhan | |
| 2010/0113311 A1 | 5/2010 | Eccleston et al. | |
| 2010/0204925 A1 | 8/2010 | Albahri | |
| 2010/0211329 A1 | 8/2010 | Farquharson et al. | |
| 2010/0218585 A1 | 9/2010 | Chawla | |
| 2011/0152136 A1 | 6/2011 | Hughes et al. | |
| 2011/0308996 A1 | 12/2011 | Choudhary | |
| 2012/0171151 A1 | 7/2012 | Thomassian | |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106028 A1 | 4/2015 | Koseoglu et al. | |
| 2015/0106029 A1 | 4/2015 | Koseoglu et al. | |
| 2015/0106031 A1 | 4/2015 | Koseoglu et al. | |
| 2015/0112610 A1 | 4/2015 | Koseoglu | |
| 2015/0112611 A1 | 4/2015 | Koseoglu | |
| 2016/0011102 A1 | 1/2016 | Koseoglu et al. | |
| 2016/0187253 A1 | 6/2016 | Koseoglu et al. | |
| 2016/0195481 A1 | 7/2016 | Koseoglu | |
| 2016/0195507 A1 | 7/2016 | Koseoglu | |
| 2016/0195508 A1 | 7/2016 | Ai-Hajji | |
| 2016/0377589 A1 | 12/2016 | Koseoglu | |
| 2017/0003217 A1 | 1/2017 | Koseoglu | |
| 2017/0363540 A1 | 12/2017 | Koseoglu | |
| 2017/0363591 A1 | 12/2017 | Koseoglu | |
| 2017/0363602 A1 | 12/2017 | Koseoglu | |
| 2017/0363603 A1 | 12/2017 | Koseoglu | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

DeFries, T. H.; Indtriz, D.; Kastrup, R. Prediction of Cetane Number by Group Additivity and Carbon-13 Nuclear Magnetic Resonance. Ind. Eng. Chem. Res. 1987, 26, 188. (Year: 1987).*

Naval Research Laboratory and Geo-Centers, Inc. Literature review of Cetane Number and its correlations (Year: 1987).*

Prasenjeet Ghosh and and Stephen B. Jaffe, Detailed Composition-Based Model for Predicting the Cetane Number of Diesel Fuels, Industrial & Engineering Chemistry Research 2006 45 (1), 346-351, DOI: 10.1021/ie0508132 (Year: 2006).*

C. Young, D & G. Galya, L. (1984). Determination of Paraffinic, Naphthenic and Aromatic Carbon in Petroleum Derived Materials by Carbon-13 NMR Spectrometry. Liquid Fuels Technology. 2. 307-326. 10.1080/07377268408915355. (Year: 1984).*

Halfdan Stenby, Erling; Yan Wei; Composition and physical properties of hydrocarbons, Encyclopaedia of Hydrocarbons (Year: 2005).*

Adhvaryu, A. et al., Quantitative NMR Spectroscopy for the Prediction of Base Oil Properties, Tribology Transactions, vol. 43, No. 2, 2000, pp. 245-250.

Albahri, T. et al, Octane Number and Aniline Point of Petroleum Fuels, 2002, Fuel Chemistry Division, vol. 47(2), pp. 710-711.

Ali, M., Resolution and Quantification of Ring Type Aromatics by HPLC Method using N-Hexane Elution, 2003, King Fahd University of Petroleum and Minerals, pp. 1-9.

ASTM D2887-01, Standard Test Method for Boiling Range Distribution of Petroleum Fractions by Gas Chromatography, Annual Book of ASTM Standards, vol. 14, No. 02, pp. 204-216.

Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).

(56) References Cited

OTHER PUBLICATIONS

Bowden, J. et al., Octane-Cetane Relationship, 1974, NTIS, p. 8.
Chemstations, Inc, Physical Properties User's Guide, 2004, Chemstations Inc., Ver. 5.4, pp. 18-22.
Cookson, D.J. et al., Investigation of the Chemical Basis of Diesel Fuel Properties, Energy & Fuels, vol. 2, No. 6, 1988, pp. 854-860.
Duvekot, C., Fast Analysis of Paraffins, iso-Paraffins, Olefins, iso-Olefins, Naphthenes and Aromatics in Hydrocarbon Streams, Varian, Inc, 2008, pp. 1-4.
Evokimov, I, et al, Potential of UV-Visible Absorption Spectroscopy for characterizing Crude Petroleum Oils, Oil an Gas Business, 2007, 21 pages.
Falla, F, et al., Characterization of crude petroleum by NIR, Journal of Petroleum Science and Engineering, vol. 51, 2006, pp. 127-137.
Fernandez-Lima, F. et al., Petroleum Crude Oil Characterization by IMS-MS and FTICR MS, 2009, American Chemical Society, Ed. 81, pp. 9941-9945.
Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.
Hasan, M.U. et al., Structural characterization of Saudi Arabian heavy crude oil by n.m.r. spectroscopy, Fuel, vol. 62, 1983, pp. 518-523.
Hidajat, K, et al., Quality characterisation of crude oils by partial least square calibration of NIR spectral profiles, Near Infrared Spectrosc, vol. 8, pp. 53-59, 2000.
Jokuty, P. et al., Hydrocarbon Groups and Their Relationships to Oil Properties and Behavior, 1995, Published by Whiticar Scientific, p. 11.
Khanmohammadi, M, et al., Characterization of petroleum-based products by infrared spectroscopyu and chemometrics, Trac Trends in Analytical Chem, vol. 35, 2012.
Kok, M, et al., High Pressure TGA analysis of crude oils, Thermochimica Acta., vol. 287, No. 1, 1996, pp. 91-99.
Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.
Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.
Pande, S., et al., Cetana Number Predictions of a Trial Index Based on Compositional Analysis, American Chemical Society, 1989, pp. 308-312.
Patra, D, et al, Determination of Synchronous Fluorescence Scan Parameters for Certain Petroleum Products, Journal of Scientific & Industrial Research, Apr. 1, 2000, pp. 300-305.
Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).
Pereira, Thieres M. C., An evaluation of the aromaticity of asphaltenes using atmospheric pressure photoionization Fourier transform ion cyclotron resonance mass spectrometry—APP ($\pm$) FT-ICR MS, Fuel, 2014, vol. 118, 2014, pp. 348-357.
Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.
Shea, T.M., Modeling Base Oil Properties using NMR Spectroscopy and Neural Networks, Tribology Transactions, vol. 46, No. 3, 2003, pp. 296-302.
Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.
Speight, Handbook of Petroleum Product Analysis, 2002.
Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.
University of Oldenburg, Institute of Physics, Catalogue of Optical Spectra of Oils, Jan. 2005, retrieved from http://las.physik.uni-oldenburg.de/data/spectra/indez.htm, 6 pages.
Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.
PCT/US2016/012115, International Search Report and Written Opinion dated May 12, 2016, 16 pages.

\* cited by examiner

CHARACTERIZATION OF CRUDE OIL BY NMR SPECTROSCOPY

RELATED APPLICATIONS

This application is a Continuation-in-Part of:

U.S. patent application Ser. No. 13/397,273 filed Feb. 15, 2012, claiming priority from U.S. Provisional Patent Application No. 61/445,175 filed Feb. 22, 2011; and PCT/US2016/012115 filed Jan. 5, 2016, claiming priority from U.S. Provisional Patent Application No. 62/099,677 filed Jan. 5, 2015, the disclosures of which are hereby incorporated by reference in their entireties.

FIELD OF THE INVENTION

This invention relates to a method and process for the evaluation of samples of crude oil and its fractions by nuclear magnetic resonance (NMR) spectroscopy.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. The compositional and property information obtained in a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

Nuclear magnetic resonance (NMR) is a property that magnetic nuclei have under a magnetic field and applied electromagnetic (EM) pulse or pulses, which causes the nuclei to absorb energy from the EM pulse and radiate this energy back out. Many scientific techniques exploit NMR phenomena to study molecular physics, crystals and non-crystalline materials through NMR spectroscopy. Nuclear magnetic resonance spectroscopy, most commonly known as NMR spectroscopy, is a technique which exploits the magnetic properties of certain nuclei.

New rapid and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining one or more indicative properties of crude oil samples are provided. Indicative properties (e.g., cetane number, pour point and cloud point, aniline point and octane number) of a gas oil fraction in crude oil samples are assigned as a function of data derived from direct NMR Spectroscopy measurement of crude oils. The correlations also provide information about the gas oil indicative properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings, in which.

DETAILED DESCRIPTION OF INVENTION

Figure 1:
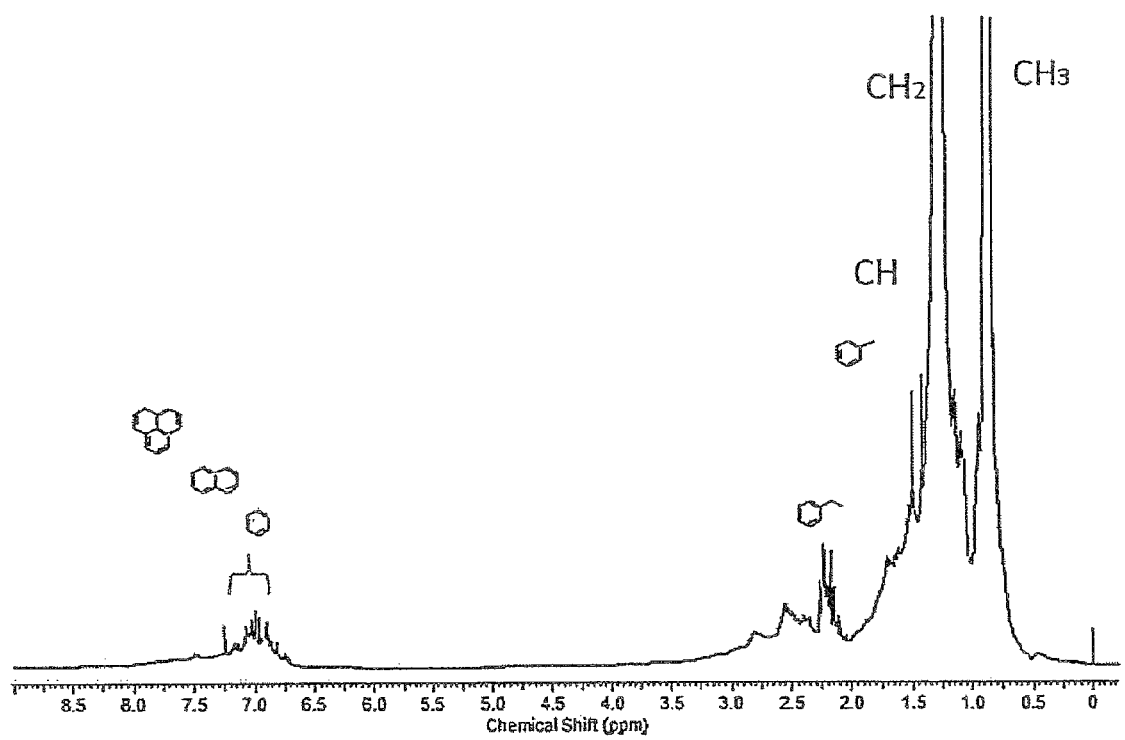
FIG. 1 is a graphic plot of $^{13}$C NMR data for the oils in a crude oil sample solution prepared as described below.

A system and method is provided for determining one or more indicative properties of a hydrocarbon sample. Indicative properties (e.g., cetane number, pour point, cloud point and aniline point) of a gas oil fraction in crude oil samples are assigned as a function of data obtained from NMR data of a crude oil sample, and in certain embodiments also the density of the crude oil sample.

The correlations provide information about gas oil and/or naphtha indicative properties without fractionation/distillation (crude oil assays) and will help producers, refiners, and marketers to benchmark the oil quality and, as a result, valuate the oils without performing the customary extensive and time-consuming crude oil assays. The currently used crude oil assay method is costly in terms of money and time. It costs about $50,000 US and takes two months to complete one assay. With the method and system herein, the crude oil can be classified as a function of NMR data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

In the system and method herein, spectra are obtained by a suitable known or to be developed nuclear magnetic resonance spectrometer. Nuclear magnetic resonance (NMR) is a property that magnetic nuclei have under a magnetic field and applied electromagnetic (EM) pulse or pulses, which causes the nuclei to absorb energy from the EM pulse and radiate this energy back out. The energy radiated back out is at a specific resonance frequency which depends on the strength of the magnetic field and other factors. This allows the observation of specific quantum mechanical magnetic properties of an atomic nucleus.

All stable isotopes that contain an odd number of protons and/or of neutrons have an intrinsic magnetic moment and angular momentum, in other words a nonzero spin, while all nuclides with even numbers of both have spin 0. The most commonly studied nuclei are $^1H$ (the most NMR-sensitive isotope after the radioactive $^3H$) and $^{13}C$, although nuclei from isotopes of many other elements (e.g. $^2H$, $^{10}B$, $^{11}B$, $^{14}N$, $^{15}N$, $^{17}O$, $^{19}F$, $^{23}Na$, $^{29}Si$, $^{31}P$, $^{35}Cl$, $^{113}Cd$, $^{129}Xe$, $^{195}Pt$) are studied by high-field NMR spectroscopy as well.

NMR is a technique for determining the structure of organic compounds. NMR is non-destructive, and with modern instruments good data can be obtained from samples weighing less than a milligram. When a sample is placed in a magnetic field, NMR active nuclei (such as $^1H$ or $^{13}C$) absorb at a frequency characteristic of the isotope. The resonant frequency, energy of the absorption and the intensity of the signal are proportional to the strength of the magnetic field. For example, in a 21 tesla magnetic field, protons resonate at 900 MHz. It is common to refer to a 21 T magnet as a 900 MHz magnet, although different nuclei resonate at a different frequency at this field strength.

Figure 2:
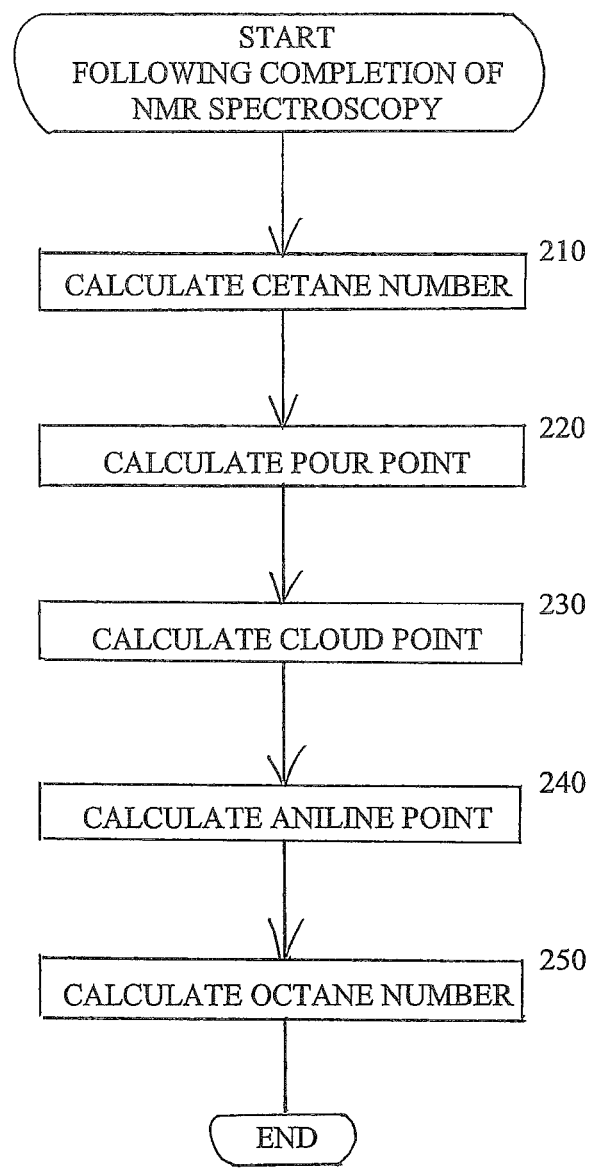
FIG. 2 is a process flow diagram of steps carried out to establish a value for indicative properties of a naphtha or gas oil fraction, using the system and method herein.

FIG. 2 shows a process flowchart of steps in a method according to one embodiment herein that occur after NMR spectroscopy is completed and the results are tabulated. In step 210, the cetane number is calculated. In step 220, the pour point is calculated. In step 230, the cloud point is calculated. In step 240, the aniline point is calculated. In step 250, the octane number is calculated. While shown sequentially in FIG. 2, the steps can be performed parallel or in any order. In certain embodiments, only one or more or steps 210, 220, 230, 240, 250 are carried out.

In a first embodiment when the only input is a $^{13}C$ NMR spectra of crude oils, one or more indicative properties (e.g., the cetane number, pour point, cloud point, aniline point and octane number) of a gas oil fraction, e.g., boiling in the range of 150-400° C. and in certain embodiments in the range of 180-370° C., are assigned as a function of the aromatic, naphthenic and paraffinic carbon content determined by $^{13}C$ NMR spectra. That is, $$\text{Indicative Property} = f(^{13}C \text{ NMR Composition}_{crude\ oil}) \quad (1);$$

Equations (2) through (6) are detailed examples of this relationship.

$$\text{Cetane Number (CET)} = X1_{CET}{}^*C_N + X2_{CET}{}^*C_P + X3_{CET}{}^*C_A + X4_{CET}{}^*C_N{}^2 + X5_{CET}{}^*C_P{}^2 + X6_{CET}{}^*C_A{}^2 \quad (2);$$

$$\text{Pour Point (PP)} = X1_{PP}{}^*C_N + X2_{PP}{}^*C_P + X3_{PP}{}^*C_A + X4_{PP}{}^*C_N{}^2 + X5_{PP}{}^*C_P{}^2 + X6_{PP}{}^*C_A{}^2 \quad (3);$$

$$\text{Cloud Point (CP)} = X1_{CP}{}^*C_N + X2_{CP}{}^*C_P + X3_{CP}{}^*C_A + X4_{CP}{}^*C_N{}^2 + X5_{CP}{}^*C_P{}^2 + X6_{CP}{}^*C_A{}^2 \quad (4);$$

$$\text{Aniline Point (AP)} = X1_{AP}{}^*C_N + X2_{AP}{}^*C_P + X3_{AP}{}^*C_A + X4_{AP}{}^*C_N{}^2 + X5_{AP}{}^*C_P{}^2 + X6_{AP}{}^*C_A{}^2 \quad (5);$$

$$\text{Octane Number (RON)} = X1_{RON}{}^*C_N + X2_{RON}{}^*C_P + X3_{RON}{}^*C_A + X4_{RON}{}^*C_N{}^2 + X5_{RON}{}^*C_P{}^2 + X6_{RON}{}^*C_A{}^2 \quad (6);$$

where:

$C_N$=CH$_3$ protons of alkyl chains γ or further from aromatic ring or CH$_3$ of saturated compounds (HSCH3);

$C_P$=CH$_2$ & CH protons of alkyl chains β or further to ring and CH$_3$ protons β to the ring (HSβ+γ);

$C_A$=Aromatic H; and $X1_{CET}$-$X6_{CET}$, $X1_{PP}$-$X6_{PP}$, $X1_{CP}$-$X6_{CP}$, $X1_{AP}$-$X6_{AP}$, and $X1_{RON}$-$X6_{RON}$ are constants.

In a second embodiment when density is considered in addition to a $^{13}C$ NMR spectra of crude oils, the indicative properties (e.g., the cetane number, pour point, cloud point, aniline point and octane number) of a gas oil fraction, e.g., boiling in the range of 150-400° C. and in certain embodiments in the range of 180-370° C., are assigned as a function of the whole crude oil density and aromatic, naphthenic and paraffinic carbon content determined by $^{13}C$ NMR spectra. That is, $$\text{Indicative Property} = f(\text{density}_{crude\ oil}, {}^{13}C \text{ NMR Composition}_{crude\ oil}) \quad (7);$$

Equations (8) through (12) are detailed examples of this relationship.

$$\text{Cetane Number (CET)} = X1_{CET}{}^*\text{DEN} + X2_{CET}{}^*C_N + X3_{CET}{}^*C_P + X4_{CET}{}^*C_A + X5_{CET}{}^*C_N{}^2 + X6_{CET}{}^*C_P{}^2 + X7_{CET}{}^*C_A{}^2 \quad (8);$$

$$\text{Pour Point (PP)} = X1_{PP}{}^*\text{DEN} + X2_{PP}{}^*C_N + X3_{PP}{}^*C_P + X4_{PP}{}^*C_A + X5_{PP}{}^*C_N{}^2 + X6_{PP}{}^*C_P{}^2 + X7_{PP}{}^*C_A{}^2 \quad (9);$$

$$\text{Cloud Point (CP)} = X1_{CP}{}^*\text{DEN} + X2_{CP}{}^*C_N + X3_{CP}{}^*C_P + X4_{CP}{}^*C_A + X5_{CP}{}^*C_N{}^2 + X6_{CP}{}^*C_P{}^2 + X7_{CP}{}^*C_A{}^2 \quad (10);$$

$$\text{Aniline Point (AP)} = X1_{AP}{}^*\text{DEN} + X2_{AP}{}^*C_N + X3_{AP}{}^*C_P + X4_{AP}{}^*C_A + X5_{AP}{}^*C_N{}^2 + X6_{AP}{}^*C_P{}^2 + X7_{AP}{}^*C_A{}^2 \quad (11);$$

$$\text{Octane Number (RON)} = X1_{RON}*\text{DEN} + X2_{RON}*C_N + X3_{RON}*C_P + X4_{RON}*C_A + X5_{RON}*C_N^2 + X6_{RON}*C_P^2 + X7_{RON}*C_A^2 \quad (12);$$

where $C_N$, $C_P$ and $C_A$ are as defined before,

DEN=density of the samples; and $X1_{CET}$-$X7_{CET}$, $X1_{PP}$-$X7_{PP}$, $X1_{CP}$-$X7_{CP}$, $X1_{AP}$-$X7_{AP}$, and $X1_{RON}$-$X7_{RON}$ are constants.

In a third embodiment when the only input is a $^1$H NMR spectra of crude oils, the indicative properties (e.g., the cetane number, pour point, cloud point, aniline point and octane number) of a gas oil fraction, e.g., boiling in the range of 150-400° C. and in certain embodiments in the range of 180-370° C., are assigned as a function of the aromatic, naphthenic and paraffinic carbon content determined by $^1$H NMR spectra. That is, $$\text{Indicative Property} = f(^1\text{H NMR Composition}_{crude\ oil}) \quad (13);$$

Equations (2) through (6) can be applied as detailed examples of this relationship, where $C_N$, $C_P$, and $C_A$ are as defined before, and $X1_{CET}$-$X6_{CET}$, $X1_{PP}$-$X6_{PP}$, $X1_{CP}$-$X6_{CP}$, $X1_{AP}$-$X6_{AP}$, and $X1_{RON}$-$X6_{RON}$ are constants.

In a fourth embodiment when density is considered in addition to a $^1$H NMR spectra of crude oils, the indicative properties (e.g., the cetane number, pour point, cloud point, aniline point and octane number) a gas oil fraction, e.g., boiling in the range of 150-400° C. and in certain embodiments in the range of 180-370° C., are assigned as a function of the whole crude oil density and aromatic, naphthenic and paraffinic carbon content determined by $^1$H NMR spectra. That is, $$\text{Indicative Property} = f(\text{density}_{crude\ oil}, ^1\text{H NMR Composition}_{crude\ oil}) \quad (14);$$

Equations (8) through (12) can be applied as detailed examples of this relationship, where $C_N$, $C_P$ and $C_A$ and DEN are as defined before, and $X1_{CET}$-$X7_{CET}$, $X1_{PP}$-$X7_{PP}$, $X1_{CP}$-$X7_{CP}$, $X1_{AP}$-$X7_{AP}$, and $X1_{RON}$-$X7_{RON}$ are constants.

Figure 3:
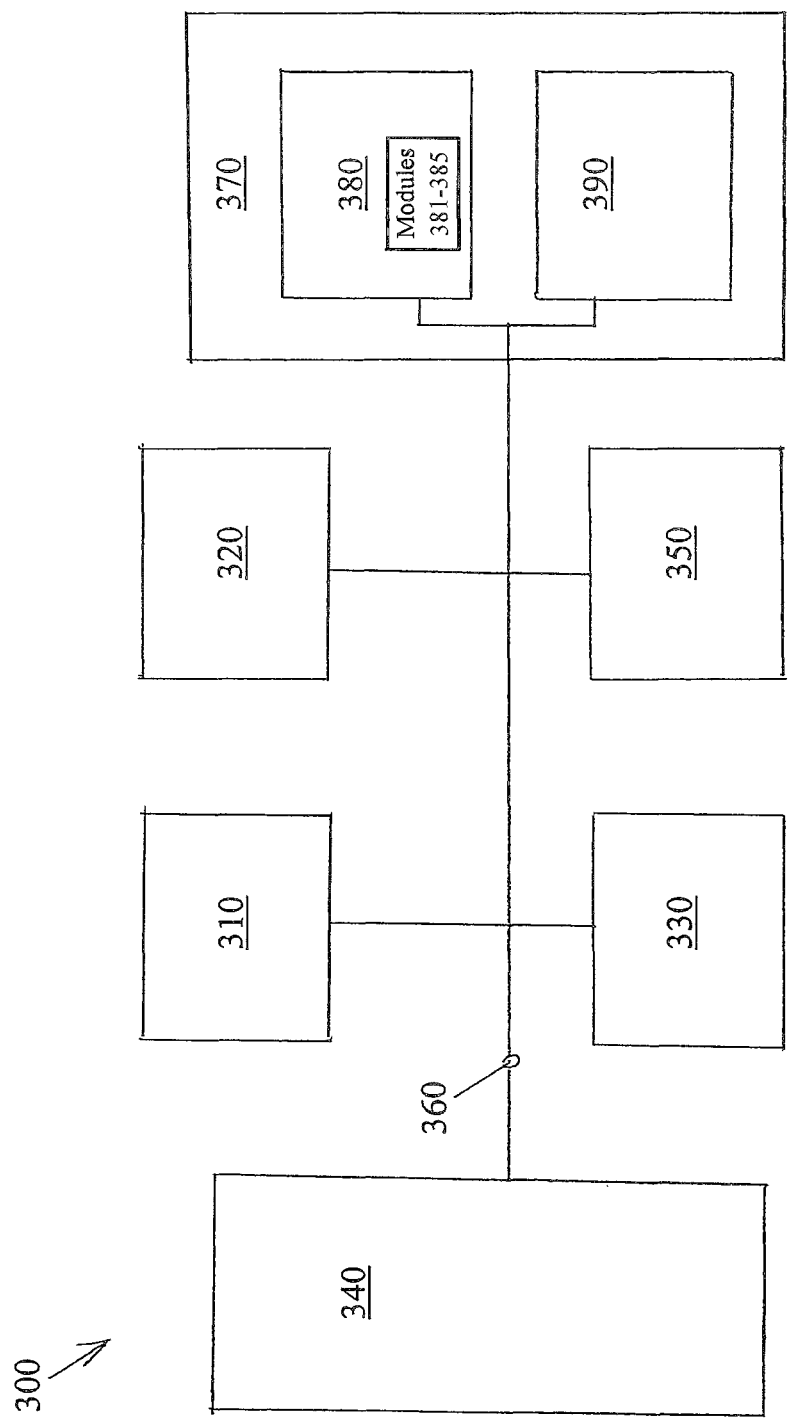
FIG. 3 is a block diagram of a component of a system for implementing the invention, according to one embodiment of the present invention.

An exemplary block diagram of a computer system 300 by which indicative property calculation modules can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores one or more indicative property calculation modules 381-385 such as cetane number calculation module 381, a pour point calculation module 382, a cloud point calculation module 383, an aniline point calculation module 384, and an octane number calculation module 385. Data storage memory 390 stores data used and/or generated by the one or more modules of the present system, including density of the crude oil sample in certain embodiments, NMR spectroscopy data or portions thereof used by the one or more modules of the present system, and calculated indicative properties generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

EXAMPLE

Crude oil solutions were analyzed by $^{13}$C and $^1$H NMR spectrometry. The quantitative NMR spectra were recorded at room temperature on a Varian VNMS 500 NMR spectrometer operating at 499.78 MHz for $^1$H and 125.67 MHz for $^{13}$C, respectively, using Dual Broadband SW/PFG probe with 5 mm 506-PP (Wilmad Glass CO., Inc.) NMR sample tubes. The NMR experiments were carried out using 40% w/v sample solution in deuterated chloroform (99.8% D, Cambridge Isotope Laboratories Inc.) with tetramethylsilane (TMS) used as an internal standard. $^1$H was performed using 16 scan numbers, 45 degree pulse length of 4.75 us, 5 s relaxation delay, 3 s acquisition time, 10 K time domain data, 15060 Hz spectra width and, 64 repetitions.

A quantitative $^{13}$C analysis was performed and an inverse gated WALTZ-16 modulated decoupling mode was used to suppress nuclear Overhauser enhancement. The experimental parameter were: 30 degree pulse length of 2.7 us with a relaxation delay of 10 s, 1.69 s acquisition time, 128 K time domain data, 35878 Hz spectra width and typical 6000 repetitions were employed. Data was processed with 5 Hz line broadening.

$^{13}$C NMR spectra were obtained for all the oils and an example of the spectra is shown in FIG. 1. As seen in this figure, the paraffinic, olefinic and aromatic carbons are identified on different regions of the spectra; the amounts of these carbons were determined by integrating the peaks identified. The carbon types were determined in the spectrum as having an aromatic region (165-100 ppm) and an aliphatic region (75-5 ppm).

As for the paraffinic and naphthenic, the 75-5 ppm region of the spectrum is used to define integrals wherever a paraffin resonance is found. In this area total paraffinic carbons are determined. It is assumed that all narrow resonances are paraffinic, and that any obvious broader NMR peak groups that represent a superposition of narrow paraffinic resonances are 100% paraffinic. The naphthenic humps were removed from the spectrum first to determine the paraffinic carbons. The difference between the total paraffinic carbon and the paraffinic carbon determined the total naphthenic carbon.

As for $^1$H NMR, the paraffinic and aromatic hydrogens were determined in the spectrum in the following regions:

| Hydrogen Type | Shift in Spectrum |
|---|---|
| Methyl ($CH_3$) protons of alkyl chains ($\gamma$) or further from the aromatic ring or methyl protons ($CH_3$) of saturated compounds ($HS_{CH3}$). | 0.5-1.0 ppm |
| Methylene ($CH_2$) and methane (CH) protons of alkyl chains ($\beta$) or further to ring and methyl ($CH_3$) protons ($\beta$) to the ring ($HS\beta + \gamma$). | 1.00-2.00 ppm |
| Aromatic proton | 6.00-10.00 ppm |

HS-Hydrogen Saturated

Exemplary constants for equations (2) through (6) for use with the first embodiment equation (1), $X1_{CET}$-$X6_{CET}$, $X1_{PP}$-$X6_{PP}$, $X1_{CP}$-$X6_{CP}$, $X1_{AP}$-$X6_{AP}$, and $X1_{RON}$-$X6_{RON}$, were developed using linear regression techniques, and are given in Table 3.

TABLE 3

|  | CET | PP | CP | AP | RON |
|---|---|---|---|---|---|
| X1 | −843.8 | −1340.0 | −797.2 | −483.6 | 1196.0 |
| X2 | 744.0 | 420.7 | 32.2 | 368.5 | −940.8 |
| X3 | 381.6 | 2053.9 | 1792.0 | 723.7 | 373.5 |
| X4 | 1149.6 | 1729.9 | 1045.6 | 699.9 | −1561.5 |
| X5 | −808.7 | −532.4 | −84.6 | −378.6 | 1075.1 |
| X6 | −954.5 | −6502.8 | −5639.8 | −2207.0 | −964.7 |

Exemplary constants for equations (8) through (12) for use with the second embodiment equation (7), $X1_{CET}$-$X7_{CET}$, $X1_{PP}$-$X7_{PP}$, $X1_{CP}$-$X7_{CP}$, $X1_{AP}$-$X7_{AP}$, and $X1_{RON}$-$X7_{RON}$, were developed using linear regression techniques, and are given in Table 4.

TABLE 4

|  | CET | PP | CP | AP | RON) |
|---|---|---|---|---|---|
| X1 | −112.8 | −213.5 | −125.9 | −91.0 | −277.5 |
| X2 | −672.8 | −1016.4 | −606.3 | −345.6 | 1562.4 |
| X3 | 995.0 | 895.7 | 312.4 | 571.0 | −321.2 |
| X4 | −282.1 | 798.0 | 1051.1 | 188.1 | −1130.1 |
| X5 | 1078.4 | 1595.2 | 966.1 | 642.5 | −1664.9 |
| X6 | −945.2 | −790.8 | −236.9 | −488.8 | 734.0 |
| X7 | 1509.4 | −1840.3 | −2889.4 | −218.6 | 4692.3 |

Exemplary constants for equations (2) through (6) for use with the third embodiment equation (13), $X1_{CET}$-$X6_{CET}$, $X1_{PP}$-$X6_{PP}$, $X1_{CP}$-$X6_{CP}$, $X1_{AP}$-$X6_{AP}$, and $X1_{RON}$-$X6_{RON}$, were developed using linear regression techniques, and are given in Table 5.

TABLE 5

|  | CET | PP | CP | AP | RON |
|---|---|---|---|---|---|
| X1 | −626.8 | −4361.5 | −2140.8 | −620.3 | 2504.3 |
| X2 | −2545.8 | −2815.3 | −3317.9 | −38.7 | −8517.3 |
| X3 | 37798.5 | 56783.6 | 50969.3 | 6716.1 | 84573.1 |
| X4 | 692.8 | 7448.9 | 3728.6 | 931.3 | −3537.2 |
| X5 | 2372.4 | 2888.7 | 3172.0 | 139.7 | 7837.1 |
| X6 | −415665.2 | −625842.1 | −561527.6 | −79178.8 | −921508.7 |

Exemplary constants for equations (8) through (12) for use with the fourth embodiment equation (14), $X1_{CET}$-$X7_{CET}$, $X1_{PP}$-$X7_{PP}$, $X1_{CP}$-$X7_{CP}$, $X1_{AP}$-$X7_{AP}$, and $X1_{RON}$-$X7_{RON}$, were developed using linear regression techniques, and are given in Table 6.

TABLE 6

|  | CET | PP | CP | AP | RON |
|---|---|---|---|---|---|
| X1 | −399.0 | −332.0 | −174.4 | −436.0 | −233.8 |
| X2 | −3093.2 | −6414.2 | −3218.8 | −3315.4 | −465.4 |
| X3 | 4465.7 | 3020.0 | −253.5 | 7622.9 | −5649.6 |
| X4 | −10114.5 | 16908.0 | 30028.9 | −45639.7 | 81342.3 |
| X5 | 4191.5 | 10360.7 | 5257.7 | 4754.4 | 1038.7 |
| X6 | −4177.3 | −2562.3 | 309.4 | −7017.3 | 5163.5 |
| X7 | 107503.5 | −190434.4 | −332876.3 | 492501.2 | −890961.9 |

The following example is provided. A sample of Arabian medium crude with a 15° C./4° C. density of 0.8828 Kg/l (e.g., at 15° C./4° C. using the method described in ASTM D4052) was analyzed by $^{13}$C NMR spectroscopy. The crude oil fractional weight composition is 0.279 naphthenic, 0.529 paraffinic, and 0.192 aromatic carbon.

Applying equation (8) and the constants from Table 4,

Cetane Number (CET)=$X1_{CET}$*DEN+$X2_{CET}$*$C_N$+ $X3_{CET}$*$C_P$+$X4_{CET}$*$C_A$+$X5_{CET}$*$C_N^2$+$X6_{CET}$*$C_P^2$+ $X7_{CET}$*$C_A^2$=(−112.8)(0.8828)+(−672.8)(0.279)+ (995.0)(0.529)+(−282.1)(0.192)+(1078.4) $(0.279)^2$+(−945.2)$(0.529)^2$+(1509.4)$(0.192)^2$

CET=60

Applying equation (9) and the constants from Table 4,

Pour Point (PP)=$X1_{PP}$*DEN+$X2_{PP}$*$C_N$+$X3_{PP}$*$C_P$+ $X4_{PP}$*$C_A$+$X5_{PP}$*$C_N^2$+$X6_{PP}$*$C_P^2$+$X7_{PP}$*$C_A^2$=(− 213.5)(0.8828)+(−1016.4)(0.279)+(895.7) (0.529)+(798.0)(0.192)+(1595.2)$(0.279)^2$+(− 790.8)$(0.529)^2$+(−1840.3)$(0.192)^2$

PP=−10° C.

Applying equation (10) and the constants from Table 4,

Cloud Point (CP)=$X1_{CP}$*DEN+$X2_{CP}$*$C_N$+$X3_{CP}$*$C_P$+ $X4_{CP}$*$C_A$+$X5_{CP}$*$C_N^2$+$X6_{CP}$*$C_P^2$+$X7_{CP}$*$C_A^2$=(− 125.9)(0.8828)+(−606.3)(0.279)+(312.4)(0.529)+ (1051.1)(0.192)+(966.1)$(0.279)^2$+(−236.9) $(0.529)^2$+(−2889.4)$(0.192)^2$

CP=−11° C.

Applying equation (11) and the constants from Table 4,

Aniline Point (AP)=$X1_{AP}$*DEN+$X2_{AP}$*$C_N$+ $X3_{AP}$*$C_P$+$X4_{AP}$*$C_A$+$X5_{AP}$*$C_N^2$+$X6_{AP}$*$C_P^2$+ $X7_{AP}$*$C_A^2$=(−91.0)(0.8828)+(−345.6)(0.279)+ (571.0)(0.529)+(188.1)(0.192)+(642.5)$(0.279)^2$+ (−488.8)$(0.529)^2$+(−218.6)$(0.192)^2$

AP=67° C.

Applying equation (12) and the constants from Table 4,

Octane Number (RON)=$X1_{RON}$*DEN+$X2_{RON}$*$C_N$+ $X3_{RON}$*$C_P$+$X4_{RON}$*$C_A$+$X5_{RON}$*$C_N^2$+

$X6_{RON}*C_P{}^2+X7_{RON}*C_A{}^2=(-277.5)(0.8828)+$
$(1562.4)(0.279)+(-321.2)(0.529)+(-1130.1)$
$(0.192)+(-1664.9)(0.279)^2+(734.0)(0.529)^2+$
$(4692.3)(0.192)^2$

RON=53

Accordingly, as shown in the above example, indicative properties including cetane number, pour point, cloud point and aniline point can be assigned to the crude oil samples without fractionation/distillation (crude oil assays).

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to *In re Beauregard*, 35 USPQ2d 1383 (U.S. Pat. No. 5,710,578), the present invention contemplates and includes this type of computer readable media within the scope of the invention. In certain embodiments, pursuant to *In re Nuuten*, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

We claim:

1. A system for assigning an indicative property to a gas oil fraction or a naphtha fraction of an oil sample, wherein the oil sample is selected from a group consisting of crude oils, bitumens, heavy oils and shale oils, the system comprising:
    a nuclear magnetic resonance (NMR) spectrometer that outputs NMR spectroscopy data;
    a non-volatile memory device that stores calculation modules and data, the data including the outputted NMR spectroscopy data indicative of aromatic, naphthenic, and paraffinic carbon content of the oil sample;
    a processor coupled to the non-volatile memory device; and
    a calculation module that calculates and assigns the indicative property of the gas oil fraction or the naphtha fraction of the oil sample as a function of the aromatic, naphthenic, and paraffinic carbon content of the oil sample, and that stores the indicative property into the non-volatile memory device, wherein the indicative property is used to determine one or more of engine/fuel performance, usability, flow characteristic, or composition of the gas oil fraction or the naphtha fraction of the oil sample.

2. The system of claim 1 wherein the calculation module calculates and assigns the indicative property of the gas oil fraction or the naphtha fraction of the oil sample as the function of the aromatic, naphthenic, and paraffinic carbon content of the oil sample, and a density of the oil sample.

3. The system of claim 2, wherein the function is a multi-variable polynomial equation with predetermined constant coefficients developed using linear regression techniques, wherein corresponding variables are aromatic carbon content, naphthenic carbon content, paraffinic carbon content and the density.

4. The system of claim 2, wherein the function is a multi-variable polynomial equation with predetermined constant coefficients developed using linear regression techniques, wherein corresponding variables are aromatic carbon content, naphthenic carbon content and paraffinic carbon content.

5. A method for assigning an indicative property to a gas oil fraction or a naphtha fraction of an oil sample, wherein the oil sample is selected from a group consisting of crude oils, bitumens, heavy oils and shale oils, the method comprising:
    preparing the oil sample for nuclear magnetic resonance (NMR) spectroscopy;
    obtaining NMR spectroscopy data indicative of aromatic, naphthenic, and paraffinic carbon content from the NMR spectroscopy of the prepared oil sample and entering the data indicative of the aromatic, naphthenic, and paraffinic carbon content into a non-volatile memory of a computer;
    using a processor of the computer to calculate and record into the non-volatile memory the indicative property of the gas oil fraction or the naphtha fraction of the oil sample as a function of the aromatic, naphthenic, and paraffinic carbon content of the oil sample, wherein the indicative property is used to determine one or more of engine/fuel performance, usability, flow characteristic, or composition of the gas oil fraction or the naphtha fraction of the oil sample.

6. The method of claim 5 further comprising calculating the indicative property of the gas oil fraction or the naphtha fraction of the oil sample as the function of the aromatic, naphthenic, and paraffinic carbon content of the oil sample, and a density of the oil sample.

7. The method of claim 6, wherein the function is a multi-variable polynomial equation with predetermined constant coefficients developed using linear regression techniques, wherein corresponding variables are aromatic carbon content, naphthenic carbon content, paraffinic carbon content and the density.

8. The method of claim 5 wherein the oil sample is crude oil.

9. The method of claim 5 wherein the oil sample is obtained from an oil well, stabilizer, extractor, or distillation tower.

10. The method of claim 5 wherein the indicative property is a cetane number.

11. The method of claim 5 wherein the indicative property is a pour point.

12. The method of claim 5 wherein the indicative property is a cloud point.

13. The method of claim 5 wherein the indicative property is an aniline point.

14. The method of claim 5 wherein the indicative property is an octane number.

15. The method of claim 5 wherein plural indicative properties are calculated including at least two indicative properties selected from a group consisting of cetane number, pour point, cloud point, aniline point and octane number.

16. The method of claim 5 wherein the NMR spectroscopy employs $^1H$ active nuclei to derive the aromatic, naphthenic and paraffinic carbon content.

17. The method of claim 5 wherein the NMR spectroscopy employs $^{13}C$ active nuclei to derive the aromatic, naphthenic and paraffinic carbon content.

18. The system or method as in claim 17 wherein the indicative property is an octane number.

19. The method of claim 5 wherein the indicative property is of the gas oil fraction boiling in a nominal range 180-370° C.

20. The method of claim 5 wherein the indicative property is of the naphtha fraction boiling in a nominal range 36-180° C.

21. The method of claim 5, wherein the function is a multi-variable polynomial equation with predetermined constant coefficients developed using linear regression techniques, wherein corresponding variables are aromatic carbon content, naphthenic carbon content and paraffinic carbon content.

* * * * *